(12) United States Patent
Scranton, Jr. et al.

(10) Patent No.: US 6,578,715 B2
(45) Date of Patent: Jun. 17, 2003

(54) PRODUCT FOR TREATING CONTAMINATED FLUIDS AND METHOD OF MAKING AND USING THE SAME

(75) Inventors: Delbert C. Scranton, Jr., Chesterfield, MO (US); Thomas G. Braga, St. Louis, MO (US)

(73) Assignee: M-I, L.L.C., Houston, TX (US)

( * ) Notice: Subject to any disclaimer, the term of this patent is extended or adjusted under 35 U.S.C. 154(b) by 0 days.

(21) Appl. No.: 09/912,199

(22) Filed: Jul. 24, 2001

(65) Prior Publication Data

US 2003/0085170 A1 May 8, 2003

(51) Int. Cl.[7] .................. B01D 24/00; B01D 39/02; B01D 39/04; B01D 39/06; C02F 1/72
(52) U.S. Cl. ................ 210/505; 210/758; 210/749; 502/400; 423/210
(58) Field of Search ............................. 502/400, 100, 502/416, 84; 504/101; 422/177, 900; 423/210; 428/905; 210/758, 749, 505

(56) References Cited

U.S. PATENT DOCUMENTS

| 4,427,630 A | * | 1/1984 | Aibe |
| 5,298,473 A | * | 3/1994 | Pinnavaia |
| 5,320,992 A | * | 6/1994 | Foc |
| 5,792,438 A | * | 8/1998 | Scranton |
| 5,997,829 A | * | 12/1999 | Sekine |
| 6,277,344 B1 | * | 8/2002 | Hei |

OTHER PUBLICATIONS

Siriwardane, patent application Publication, US 2002/0052291 A1, May 2, 2002.*

* cited by examiner

Primary Examiner—W. L. Walker
Assistant Examiner—K S Menon
(74) Attorney, Agent, or Firm—Thompson Colburn LLP (57) ABSTRACT

A product, capable of treating contaminated fluids, preferably gases, is disclosed. The product contains a carrier, an activated metal oxide, an odor counteractant, a carrier for the odor counteractant, and an agent which limits diffusion of the odor counteractant. The product removes sulfur contaminants, such as hydrogen sulfide and mercaptans, while also reducing and/or neutralizing other common odor causing compounds in fluids, preferably gases. Methods of making and using the product are also disclosed.

21 Claims, 4 Drawing Sheets

Reduction of H2S using Mulch with 20% (wt) Iron Oxide/Cuprous Oxide Composition

Fig. 1: Comparison of H2S Removal of "Dry" and "Wet" Mulch.

Fig. 2: Reduction of $H_2S$ using Mulch without Additive

Fig. 3: Reduction of $H_2S$ using Mulch with 2%(wt) Iron Oxide/ Cuprous Oxide Composition Fig. 4: Reduction of $H_2S$ using Mulch with 5%(wt) Iron Oxide/ Cuprous Oxide Composition Fig. 5: Reduction of $H_2S$ using Mulch with 10%(wt) Iron Oxide/ Cuprous Oxide Composition Fig. 6: Reduction of H2S using Mulch with 20% (wt) Iron Oxide/Cuprous Oxide Composition Fig. 7: Pressure Drop as Function of Velocity

PRODUCT FOR TREATING CONTAMINATED FLUIDS AND METHOD OF MAKING AND USING THE SAME

FIELD OF INVENTION

The present invention relates to a product for use in controlling and treating odiferous contaminants. Specifically, the invention relates to a product for use in removing sulfur contaminants, such as hydrogen sulfide and mercaptans, while neutralizing many other common odor causing compounds in sewage gas, and a method for making and using the same.

BACKGROUND OF INVENTION

Sewer systems and similar structures, typically contain organic waste and harbor standing pools of water. It is known that bacteria thrive in conditions where adequate moisture and food (organic waste) are present. Many of these bacteria essentially convert the waste into contaminated gas. Additionally, the breakdown of the waste will also release contaminants. Hydrogen sulfide ($H_2S$), mercaptans and other sulfur contaminants found in such gas, cause the gas to have a foul smell. This contaminated gas will collect due to bacteria growth in the sewer system, excessive moisture, the environment itself, and various other odor causing entities. The gas containing the odiferous contaminants will exit the sewer system causing malodors in the nearby environment.

Currently, most products for reducing or eliminating odors in a sewer system are either biofilters or are carbon-based. Biofilters use organic materials, which allow for the growth of bacteria, to reduce odors. The bacteria in these products reduce or eliminate the odors in the sewage gas. Biofilters are comparatively slow systems. The bacteria in biofilters require near 100% relative humidity in order to optimize their ability to reduce or eliminate sewage gas odors. In order to work immediately, a biofilter must be seeded with bacteria. If not seeded, the biofilter will not be able to remove hydrogen sulfide and mercaptans until bacteria grow on the biofilter. In contrast, carbon-based products require a relative humidity of near 80% or less in order to absorb hydrogen sulfide and mercaptans at a rate ranging between about 5% by weight of the carbon-based product and about 20% by weight of the carbon-based product. In conditions of high relative humidity (over 80% relative humidity), the carbon-based products absorb the water in the air. This absorption of water saturates the carbon and, therefore, inhibits absorption of hydrogen sulfide and mercaptans. Further, carbon-based products are hazardous once impregnated with the hydrogen sulfide and mercaptans.

What is desired is a product that will successfully neutralize or treat various odors found in contaminated gas, including methane, hydrogen sulfide, and ammonia. This product should preferably be capable of removing hydrogen sulfide under any of a variety of relative humidity conditions, and have increased efficiency with regards to the removal of hydrogen sulfide, while not significantly increasing the media pressure drop throughout the system. Further, the product should be able to remove the hydrogen sulfide as soon as the product is in place. The increased efficiency of the product should allow for smaller filter sizes.

SUMMARY OF INVENTION

The present invention relates to a product for treating contaminated fluids, preferably gas, and methods for making and using the same. In particular, the present invention is used for treating gases contaminated with sulfur compounds, whereby such contaminated gases emanate from a sewer or similar structure. The product is comprised of a carrier, preferably mulch, and a metal oxide, preferably an activated metal oxide. It is further preferred for such product to include an odor counteractant, a carrier for the odor counteractant, and an agent, which limits the diffusion of the odor counteractant. The product can be placed in a vessel or similar member in a position proximate to where the contaminated gas exits the system where such contaminated gas was generated. More importantly, the product should be placed in a position to filter contaminated gas.

Contaminated sewage gas typically exits a sewer through a manhole. As such, a vessel placed in the neck of a manhole may be used. As the contaminated sewage gas passes through the vessel, the product reacts with and removes sulfur contaminants from the contaminated sewage gas, while neutralizing or treating various other malodors commonly found in sewer systems.

The product removes or neutralizes the odor contaminants found in the gas by contacting such gas with reactive constituents found in the product. The metal oxide of the product will react with the sulfur contaminants in the gas so that the contaminants are substantially eliminated from the gas. The product will also release constituents, which neutralize some of the malodors found in the gas. The product includes a carrier, preferably mulch, which helps to absorb moisture. The carrier may further include non-organic matter, such as porous styrofoam for void support and nutrients.

Mulch, which usually functions as a protective ground covering that helps retain moisture in the soil, is most often made of organic matter such as wood products, compost, leaves, straw, bark, soil, clay, carbon, limestone, shale, volcanic rock, and combinations thereof. Mulch is advantageous as a carrier because it supports limited bacterial growth, absorbs some odiferous contaminants to eliminate them from the gas, and has a very porous surface, so it readily absorbs and holds moisture. A further advantage of mulch is its large surface area, which is desired because it provides an increased surface area for contacting the contaminated gas and provides more surface area for holding constituents for treating the odors. Bark mulch is most preferred because it offers a larger surface area compared to other available mulches, and is slow to degrade.

A product reactive with sulfur compounds, preferably metal oxide, is also present in the product. The metal oxide reacts with various sulfur compounds in the contaminated fluids, preferably gas, to remove hydrogen sulfide, mercaptans, and other sulfur contaminants. It is preferred if the metal oxide is activated. It is especially preferred to use an iron oxide activated with copper oxides or manganese oxides.

The third preferred constituent is an odor counteractant, which neutralizes or reduces the perceived odor levels of various malodors present in sewage gas. The odor counteractant reduces the perceived odor of malodors by possessing a virtually identical molecular configuration (size and weight) as the malodors. Malodors tend to have simple molecular forms with approximately 90% of them originating from a small group of chemicals with similar molecular structures. The odor counteractant has a virtually identical molecular configuration as the malodors and, therefore, binds to the malodor receptor sites. The odor counteractant is able to bind to malodor receptor sites in a person's olfactory system and prevent the receptor sites from receiving any malodor molecules. Thus, the binding of the odor counteractant to the malodor receptor site neutralizes the malodor and creates the perception of the area being odor free or pleasant to smell. By blocking malodors, odor counteractants eliminate the need for masking odors. The odor counteractants are placed on a carrier for the odor counteractant and combined with the carrier and metal oxide composition to form the product.

The carrier for the odor counteractant is present to limit contact between the odor counteractant and the metal oxide. The carrier for the odor counteractant does not have to be organic. This carrier can be clay, mulch, shale, carbon, porous styrofoam, porous ceramic or any other material, which is absorbent and porous. The odor counteractants are known to react with the metal oxide, thereby reducing the product life. By mixing the odor counteractant with the carrier for the odor counteractant prior to mixing with the carrier and metal oxide composition, the odor counteractant is separated from the metal oxide thereby blocking its reaction with the metal oxide, thus increasing the product life.

The odor counteractant is extremely volatile when mixed with the carrier by itself. Therefore, an agent which limits diffusion of the odor counteractant is added to the odor counteractant and carrier composition. This lowers the volatility of the odor counteractant, thereby further lengthening the product life. Without the addition of this agent, the product life is about a month. Upon the addition of this agent, the product life is increased up to several years.

The product can be made by combining the metal oxide and an activator to produce an activated metal oxide, and combining the carrier for the odor counteractant with the odor counteractant and the agent which limits diffusion of the odor counteractant to form an odor counteractant and carrier composition. These compositions are then mixed with the carrier to produce the final product.

The product's increased efficiency at removing sulfur contaminants is an advantage over current carbon-based products. The product removes the sulfur contaminants without causing a significant media pressure drop. This is an advantage over soil and compost biofilter products. Media pressure is defined as the resistance to fluid flow through the media. As the materials in biofilters compact over time, a media pressure drop occurs. This is especially prevalent in biofilters made from soil, compost, or other highly compactable materials.

Increased efficiency is further achieved by chemically treating the sewage gas through the use of metal oxides while, at the same time, treating the sewage gas biologically with bacteria and neutralizing malodors through the odor counteractant. Current systems either treat the sewage gas biologically or absorb the gas, which leads to a hazardous end material. Most current systems do not chemically react with sulfur compounds. Another advantage is the increased surface area of the product, as compared to carbon-based products. This increased surface area provides an increased surface for contact with the contaminated gas. The increased surface area also provides more capacity for holding constituents, which neutralize or treat malodors.

The increased efficiency at removing sulfur contaminants, along with the increased surface area, allow for the use of smaller filter sizes when using the product. Thus, the product can readily be used in small areas.

A further advantage is that the product neutralizes or treats various malodors found in contaminated gas, while removing the sulfur contaminants. Also, the product works at any relative humidity. Finally, the comparatively light weight of the product makes it easy to work with and easy to mix, once the product is placed in a filter.

DETAILED DESCRIPTION

The present invention relates to a product, preferably a mulch product, for treating contaminated fluids, especially gases, and methods of making and using this product. The increased efficiency at removing sulfur contaminants and other odiferous constituents from contaminated sewage gas is achieved by relying on simultaneous chemical treatment and biological treatment of the contaminated sewage gas. Although sewage gas is specifically mentioned, this product is not limited to use with contaminated sewage gas. It will also work in a gas trap or other situations where sulfur contaminated gas is present. Increased efficiency in hydrogen sulfide removal allows for the use of a comparatively smaller filter device.

The product substantially removes sulfur contaminants, in particular, hydrogen sulfide, from contaminated fluid. The contaminated fluid can have up to 200 parts per million (ppm) of hydrogen sulfide. Further, the contaminated fluid may include spikes of 2,000 ppm of hydrogen sulfide, with these spikes lasting less than two hours at a time. The product can reduce these hydrogen sulfide levels to non-detectable levels for a significant portion of the product life. KITAGAWA® (manufactured by Komyo Nikagaku, Kogyo K. K. Japan) hydrogen sulfide detection tubes are used to determine hydrogen sulfide levels in the contaminated fluids. Later in the product life, the hydrogen sulfide levels are reduced to no more than 10 ppm. The product life depends upon the moisture content of the product, the size of the vessel, which contains the product, and the amount of hydrogen sulfide removed by the product.

The product results in reductions of hydrogen sulfide levels in the contaminated fluid to between about 20% and about 99% of original levels, depending on the requirements of the environment. The preferred range of reduction of hydrogen sulfide levels is between about 50% and about 99% of original levels. The product also efficiently removes, or neutralizes, odiferous constituents found in the contaminated fluid emanating from sewers and like structures. Further, this product works at any relative humidity.

A significant increase in the media pressure drop does not occur with the present product. Media pressure is the resistance to fluid flow through the media. It is important that a media pressure drop is not observed so that excess energy is not required to reduce hydrogen sulfide levels in the contaminated sewage gas.

The product is formed from a substrate carrier, a metal oxide, an odor counteractant, a carrier for the odor counteractant, and an agent which limits diffusion of the odor counteractant. The substrate carrier is preferably organic. Additional constituents can be included. The metal oxide is preferably activated. Also, the substrate carrier is preferably a mulch type product.

Any substrate can be used that will hold or carry the metal oxide. The carrier should be porous so that it can readily absorb and hold moisture. Absorption of moisture is important to maintain the reactivity of the metal oxide. Also, absorption capacity can be useful in eliminating some malodorous compounds, as absorption will allow bacteria to contact contaminants. If the substrate dries out prior to being mixed with the metal oxide, water should be added to the substrate in an amount equal to between about 1% by weight of the product and about 75% by weight of the product. Retention of moisture is also desired to promote limited bacteria growth, as some bacteria react with and treat contaminants found in the gas. Porosity sufficient to allow the passage of fluids, especially gas, is an important characteristic of the carrier.

The comparatively lighter weight of the present carrier makes it easier to turn or mix the product of this invention. This comparatively lighter weight also makes for easier overall use. The carrier can be any of a variety of organic materials, especially mulch. Mulch includes bark, compost, leaves, straw, soil, clay, carbon, limestone, shale, volcanic rock, wood products, and combinations thereof. Wood products include shredded wood, wood particles, wood chips, sawdust, and combinations thereof. The carrier is preferably comprised of organic material; however, some non-organic material may be included in the carrier for void support and nutrients. This non-organic material includes porous styrofoam. The most preferred mulch for this product is bark mulch due to its large surface area and because it does not readily degrade.

As the contaminated sewage gas passes over and through the product, the carrier absorbs some of the evaporated moisture in the contaminated sewage gas. The use of mulch is preferred because the mulch absorbs moisture, thereby increasing the growth of bacteria in the mulch, which helps to reduce and eliminate some malodors in the contaminated sewage gas. A further advantage of mulch is its large surface area, which provides a larger area for the contaminated fluid, preferably gas, to pass over. The mulch offers an increased surface area as compared to currently used carbon-based products. This increases the overall contact time of the contaminated gas with the product thereby increasing the likelihood that the contaminated gas will come into contact with the other constituents of the product and be decontaminated.

The carrier is present in the product of the present invention in an amount equal to between about 25% and about 98% by weight of the product. Preferably the carrier is present in an amount equal to between about 30% and about 80% by weight of the product, and more preferably in an amount equal to between about 50% and about 75% by weight of the product.

The metal oxide reacts with and removes sulfur contaminants, including oxides of sulfur, hydrogen sulfide, and thiols from the contaminated fluid, preferably gas. The presence of the metal oxide in the product ensures that the product begins to work immediately after being placed in a contaminated environment. The metal oxide can be iron oxide, iron hydroxide, zinc oxide, zinc hydroxide, manganese oxide, manganese hydroxide, and combinations thereof. The use of iron oxide is preferred, with the iron oxide being selected from the group including FeO, $Fe_2O_3$, $Fe_3O_4$, hydrated forms of iron oxide, and combinations thereof.

The metal oxide is preferably activated. The activator increases the rate of reactivity of the metal oxide with sulfur compounds contained in fluids. This allows the metal oxide to remove sulfur compounds more quickly and efficiently. Preferably, the activator will have a higher electro-potential than the metal oxide so that when the activator is coupled with the metal oxide the coupling will result in an increase in the reactivity of the metal oxide with sulfur compounds contained in fluids. The activator is further defined in U.S. Pat. No. 6,251,348, issued Jun. 26, 2001, and herein incorporated by reference.

The activator is added to the metal oxide in an amount equal to between about 0.1% and about 20% by weight of the product. Preferably, the activator is used in an amount equal to between about 0.25% and about 5% by weight of the product. Larger amounts of the activator, greater than 5% by weight of the product can be used; however, it is most preferred to use an amount of activator equal to approximately 3% by weight of the product. The activator is typically a more noble metal, such as copper, platinum, gold, silver, cadmium, nickel, palladium, lead, mercury, tin, cobalt, manganese, oxides of these metals, carbonates of these metals, and combinations thereof. The use of small amounts of copper species and/or manganese species is preferred because they are readily available and meet current environmental standards as promulgated by the Environmental Protection Agency. Suitable copper species include copper compounds such as copper metals, copper oxides, copper carbonates, any copper salt, and copper alloys. While suitable, manganese species include manganese oxides, manganese carbonates, manganese metals, any manganese salt, and manganese alloys. When manganese is the metal oxide, an activator other than those in the manganese species should be used.

The metal oxide, regardless of whether it is activated, is present in the product in an amount equal to between about 2% and about 75% by weight of the product. Preferably, in an amount equal to between about 20% and about 50% by weight of the product, and more preferably equal to between about 35% and about 50% by weight of the product.

The activated metal oxide composition can be added to the carrier as one component or the activator and metal oxide can be added separately. After addition of the activated metal oxide, the carrier is thoroughly mixed to incorporate the activated metal oxide throughout the carrier.

A carrier for the odor counteractant is used to keep the odor counteractant from contacting the metal oxide. Reactions between the metal oxide and the odor counteractant are decreased when a carrier for the odor counteractant is used, thereby reducing the likelihood of a shortened product life. In the absence of the carrier for the odor counteractant, the essential oils, mineral acids, esters, organic acids, and alkalines used as odor counteractants, tend to react with the metal oxides. Such a reaction decreases the reactivity of the metal oxide with the sulfur compounds and, thus, decreases the overall removal rate of the hydrogen sulfide. The carrier for the odor counteractant is present in the product in an amount equal to between about 1% and about 70% by weight of the product. Preferably, the carrier for the odor counteractant is between about 5% and about 50% by weight of the product. The carrier can be any organic or inorganic material that is absorbent and porous. This includes clay, mulch (as defined above), porous styrofoam, carbon, shale, and porous ceramic. A 4×16 mesh clay, which is large grained, calcined clay, is preferred for use in the present product.

The odor counteractant of the product produces a perception of an "odor-free" environment. The odor counteractant is designed to have a virtually identical molecular configuration as the malodors. This allows the odor counteractant to bind to malodor receptor sites in a person's olfactory system, thereby competing with and blocking the malodors from binding to these receptor sites. This neutralizes the malodors, thus giving the perception of the area being odor free or pleasant to smell. The odor counteractant is present in the product in an amount equal to between about 0.1% and about 40% by weight of the product. Preferably, the odor counteractant is present in the product in an amount equal to between about 1% and about 20% by weight of the product. The present invention relies on the use of essential oils, esters, mineral acids, organic acids, alkalines, and combinations thereof as odor counteractants; however, other odor counteractants may be used. An essential oil is defined as a volatile oil derived from the leaves, stem, flower, or twigs of plants, and usually carries the odor or flavor of the plant. Essential oils include floral oils, such as green floral and rose floral, spice oils, such as sage oil, and citrus oils, such as lemon oil, lime oil, orange oil, and grapefruit oil. These essential oils include natural and synthetically made essential oils. Alkalines are chemical substances, which neutralize acids. Alkalines include baking soda, limestone, magnesium oxides, and magnesium hydroxides.

When the odor counteractant is placed on the carrier for the odor counteractant, the odor counteractant is absorbed by the carrier and quickly volatizes into the air. This limits the effect of the odor counteractant to between one week and one month. However, the volatility of the odor counteractant can be slowed by placing the odor counteractant on the carrier but not to the point of saturation. Next, an agent, which limits diffusion of the odor counteractant is added to saturate the carrier in order to limit volitization of the organic reactants.

The agent, which limits diffusion of the odor counteractant, should be able to prevent rapid volatilization of the odor counteractant. This agent includes water, glycols, such as propylene glycol, diluents, and combinations thereof. A diluent is an ingredient used to reduce the concentration of an active material to achieve a desirable and beneficial effect. As the odor counteractants tend to be hydrophobic, water is the preferred agent. The water molecules act as a seal around the carrier, trapping the hydrophobic odor counteractant inside the carrier, thereby slowing down its rate of release from the carrier and prolonging the life of the product. By saturating the carrier for the odor counteractant, the agent helps to provide a less volatile, more controlled and diluted release of the odor counteractant. This increases the product life to months or even years. The amount of agent added is equal to between about 1% by weight of the product and 75% by weight of the product. The key is the saturation of the carrier for the odor counteractant. This slows the volatility of the odor counteractant. Saturation is defined as fully saturating the carrier, or adding enough moisture to coat the surface of the carrier and, thereby, inhibit volatilization of the odor counteractant.

The amount of the agent added is dependent on the saturation point of the carrier and the amount of odor counteractant added to the carrier. When larger amounts of odor counteractants are added to the carrier, less of the agent is required to reach the saturation point of the carrier. The addition of smaller amounts of odor counteractant to the carrier will require the addition of greater amounts of the agent to saturate the carrier. This composition of odor counteractant, carrier, and agent which limits diffusion of the odor counteractant is then combined with the carrier and metal oxide composition to form the product of this invention. An odor masking agent may, in the alternative, be used in place of the odor counteractant.

The product can be used to treat fluids, preferably gas, by passing the gas over and through the product. Fluids include liquids, gases and mixtures thereof. The product works in ambient temperature, with ambient temperature defined as between about 32° F. and about 200° F. This product can be used under any relative humidity conditions. As the gas comes in contact with the product, the undesirable odors are dissipated and the sulfur contaminants of the gas are reacted with the metal oxide, thereby reducing the total amount of sulfur. The product can be placed in a vessel constructed to allow the contaminated fluid to pass through the vessel and contact the product, thereby treating and decontaminating the contaminated fluid. In a preferred embodiment, the product of this invention is placed in a vessel which fits in a sewer manhole, so that the product is available to treat contaminated sewage gas, which passes through the vessel.

The method of making the product involves mixing all the constituents in ambient temperature to achieve a homogenous mix. The amount of each constituent can be varied within the ranges disclosed above, depending on the hydrogen sulfide levels of the contaminated fluids and the levels of the various malodors. For example, a high level of hydrogen sulfides in a contaminated gas containing low levels of malodors would require the product to include higher amounts of the metal oxide (about 75% by weight of the product), and less odor counteractant (about 0.1% by weight of the product). Any of a variety of devices can be used to mix the products, including paddle mixers, tumblers, and a variety of other mixers.

EXAMPLES

Example 1

"Dry" and "Wet" Mulch without Additives

Two compositions for treating sewage gases were formed. Both compositions were formed from bark mulch. The "dry" bark mulch was used as the first composition for treating sewage gases and had 36% water by weight of the mulch. The second composition, or "wet" mulch, was formed by soaking the mulch in water for one hour, and shaking it to remove excess water. The "wet" mulch contained approximately 57% water by weight of the mulch. These compositions are representative of biofilters as currently used. The "wet" mulch should have more bacteria present, compared to the "dry" mulch.

Each type of mulch was separately placed in a 3.75" vessel and tested as described below. Compressed air containing hydrogen sulfide at levels of 10–25 (ppm) was kept in a storage tank. The actual amount of hydrogen sulfide in the compressed air was determined using GASTEC® (manufactured by Gastec, Corp.), or KITAGAWA® (manufactured by Komyo Rikagaku, Kogyo K. K. Japan), hydrogen sulfide detection tubes. The compressed air was used within four (4) hours in order to limit the reduction in hydrogen sulfide levels due to oxidation.

The storage tank was attached to a needle valve and a flowmeter. The flowmeter was attached to the 3.75" vessel. The vessel, further included a bed support, an access fitting for pressure drop measurements, and an air outlet. The access fitting was included on the vessel to allow pressure to be measured as the air passed through the vessel. It is important that a pressure drop is not seen. If a pressure drop occurs, excess energy must be added to the system in order to allow the mulch product to continue to remove the hydrogen sulfide from the sewage gas.

The needle valve was opened to allow the compressed air to pass from the storage tank into the flowmeter, where the rate of the airflow was measured. The hydrogen sulfide levels in the compressed air were recorded prior to the compressed air entering the vessel. The compressed air then passed into the vessel. Once in the vessel, the compressed air passed through the bed support and then on through the mulch product, exiting at the air outlet at the opposite end of the vessel. Hydrogen sulfide levels in the compressed air were recorded prior to the compressed air leaving the vessel.

Figure 1:
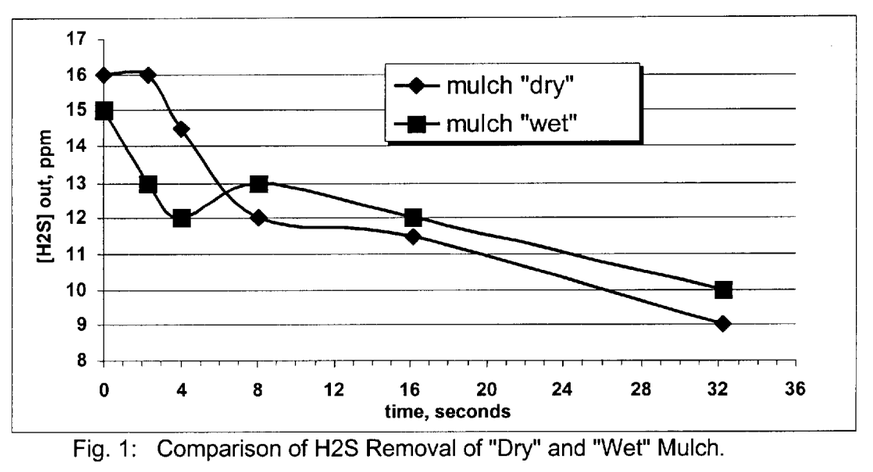
FIG. 1 is a graph showing comparison of hydrogen sulfide removal of "dry" and "wet" mulch.
Figure 2:
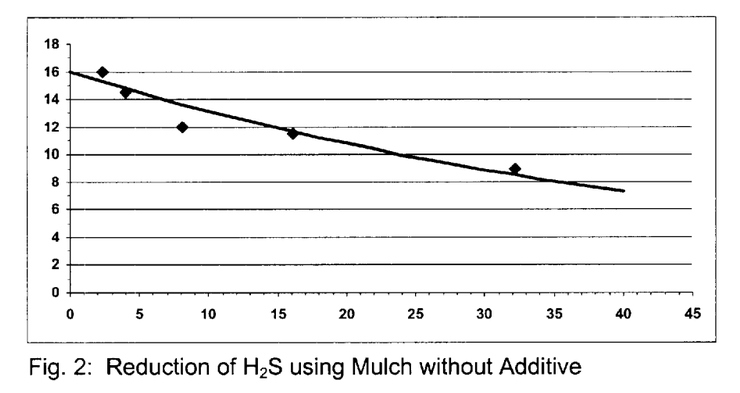
FIG. 2 is a graph indicating reduction of hydrogen sulfide using mulch without additive.

The results of using the "dry" and "wet" mulch are shown in Table 1 and FIG. 2. The results indicate that the mulch, by itself, is not extremely reactive with the hydrogen sulfide. As such, the "stand alone" mulch requires a greater reaction time when compared to commonly reported contact times. The addition of more than 35% water in the as received "dry" mulch does not have any effect on the removal rate, as compared to the "wet" mulch. Finally, the removal, as a function of time, appears to follow an exponential function. As can be seen in Tables 1 and 3, limited hydrogen sulfide removal did occur.

TABLE I

| Material | Bed Height Feet | Flow Feet$^3$ per minute (cfm) | Residence Time, sec. | (H$_2$S) in ppm | (H$_2$S) out ppm |
|---|---|---|---|---|---|
| Mulch "dry" | 1.75 | 3.5 | 2.3 | 16 | 16 |
| Mulch "dry" | 1.75 | 2.0 | 4.0 | 16 | 14.5 |
| Mulch "dry" | 1.75 | 1.0 | 8.1 | 16 | 12 |
| Mulch "dry" | 0.75 | 0.4 | 8.6 | 16 | 16 |
| Mulch "dry" | 1.75 | 0.5 | 16.1 | 16 | 11.5 |
| Mulch "dry" | 1.75 | 0.3 | 32.2 | 16 | 9 |
| Mulch "wet" | 1.75 | 3.5 | 2.3 | 15 | 13 |
| Mulch "wet" | 1.75 | 2.0 | 4.0 | 15 | 12 |
| Mulch "wet" | 1.75 | 1.0 | 8.1 | 15 | 13 |
| Mulch "wet" | 1.75 | 0.5 | 16.1 | 15 | 12 |
| Mulch "wet" | 1.75 | 0.3 | 32.2 | 15 | 10 |

Example 2

Mulch Products Prepared Containing 2%, 5%, 10% and 20% by Weight of Activated Metal Oxide.

Four compositions for treating sewage gases were formed. All four compositions were formed from an activated metal oxide and a mulch carrier. Each composition was admixed until a homogenous mulch/metal oxide mixture was achieved. The iron oxide/cuprous oxide composition was distributed into the bark mulch by gradually adding the necessary amount, in small portions, while shaking to ensure mixture with the mulch between additions of the iron oxide/cuprous oxide composition. All the products were separately placed in a 3.75" vessel and tested according to the procedure disclosed in Example 1.

Figure 3:
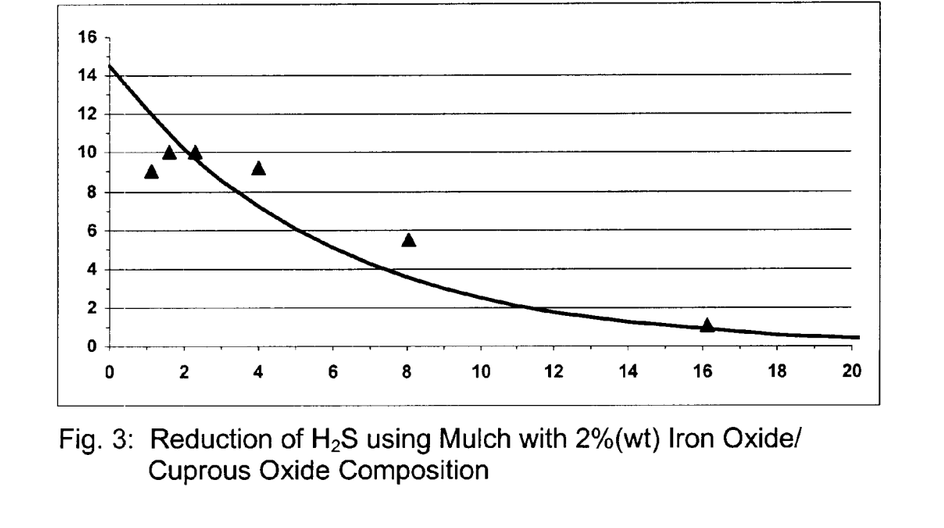
FIG. 3 is a graph indicating reduction of hydrogen sulfide using mulch with 2% (wt) iron oxide/cuprous oxide composition.

Table 2 and FIG. 3 indicate the results of the reduction of hydrogen sulfide, using mulch with 2% (wt) iron oxide/cuprous oxide composition. The calculated removal time, as a function of percent iron oxide/cuprous oxide composition was 50% removal within 4 seconds, and 90% removal time within 13 seconds (see Table 3).

FIGS. 3–6 are graphs indicating the reduction of hydrogen sulfide in Example 2 of the present application. The curves on the graphs of FIGS. 3 through 6 were developed using a fitting equation for an exponential rate law decay curve. The same fitting equation was used for each composition.

Figure 4:
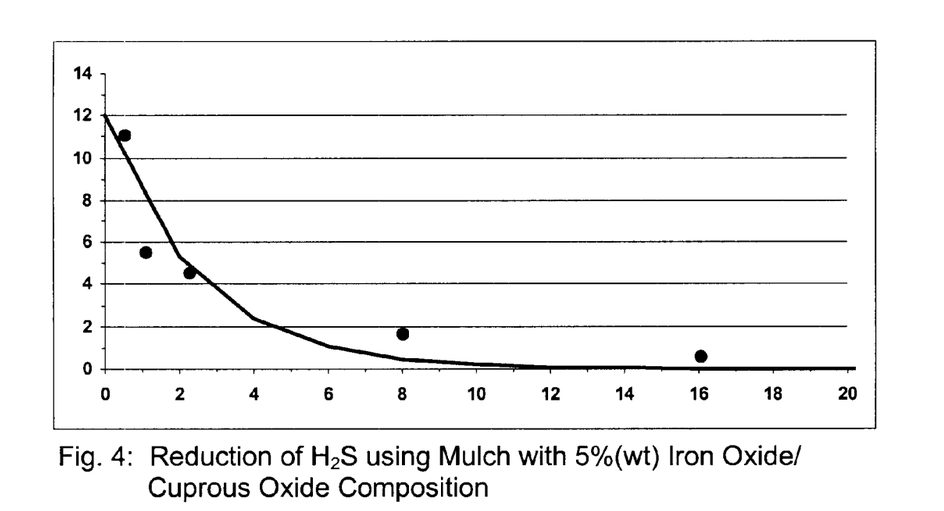
FIG. 4 is a graph indicating reduction of hydrogen sulfide using mulch with 5% (wt) iron oxide/cuprous oxide composition.

Table 2 and FIG. 4 indicate the reduction of hydrogen sulfide, using a mulch product with a 5% (wt) iron oxide/cuprous oxide composition. The calculated removal time as a function of percent iron oxide/cuprous oxide for this Example was 50% removal at time 1.7 seconds, and 90% removal at time 5.6 seconds (see Table 3).

Figure 5:
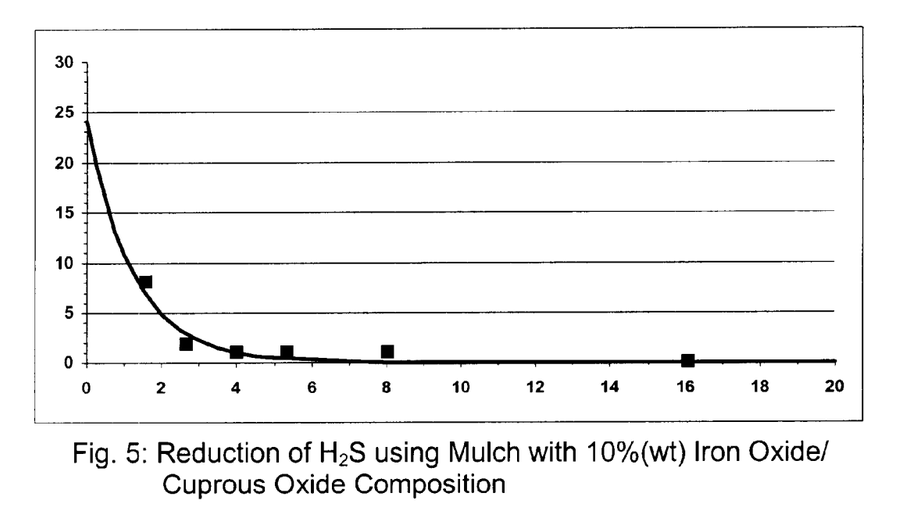
FIG. 5 is a graph indicating reduction of hydrogen sulfide using mulch with 10% (wt) iron oxide/cuprous oxide composition.

Table 2 and FIG. 5 indicate the reduction of hydrogen sulfide, using mulch with 10% (wt) iron oxide/cuprous oxide composition. The calculated removal time as a function of percent iron oxide and cuprous oxide is 50% removal at time 0.9 seconds, and 90% removal at time 2.9 seconds (see Table 3).

Figure 6:
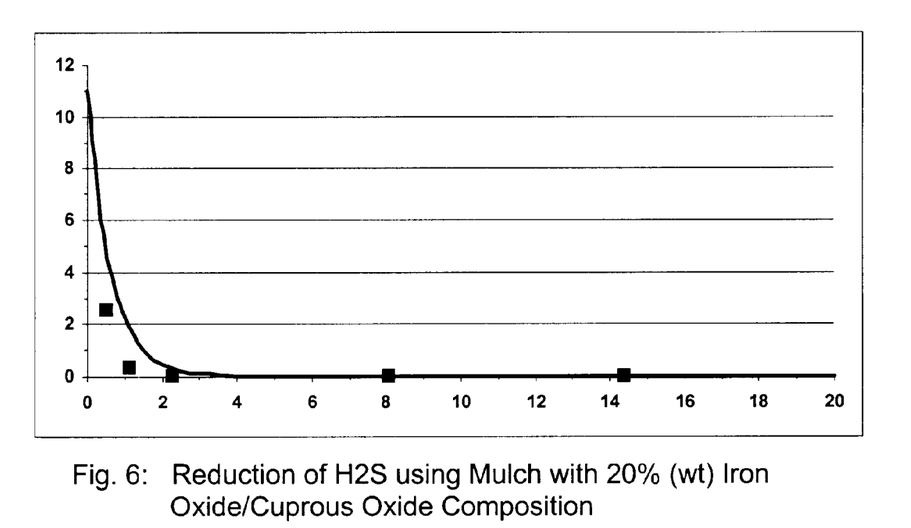
FIG. 6 is a graph indicating reduction of hydrogen sulfide using mulch with 20% (wt) iron oxide/cuprous oxide composition; and, FIG. 7 is a graph indicating pressure drop as a function of velocity.

Table 2 and FIG. 6 indicate the reduction of hydrogen sulfide, using mulch with 20% (wt) iron oxide/cuprous oxide composition. The calculated removal time as a function of percent iron oxide/cuprous oxide is 50% removal at time 0.3 seconds, and 90% removal at time 1.2 seconds (see Table 3).

TABLE 2

| Material | Bed Height Feet | Flow cfm | Residence Time, sec. | (H$_2$S) in ppm | (H$_2$S) out ppm |
|---|---|---|---|---|---|
| mulch + 2 wt % metal oxide composition | 1.75 | 7.0 | 1.2 | 14.5 | 9 |
| mulch + 2 wt % metal oxide composition | 1.75 | 5.0 | 1.6 | 14.5 | 10 |
| mulch + 2 wt % metal oxide composition | 1.75 | 3.5 | 2.3 | 14.5 | 10 |
| mulch + 2 wt % metal oxide composition | 1.75 | 2.0 | 4.0 | 14.5 | 9.2 |
| mulch + 2 wt % metal oxide composition | 1.75 | 1.0 | 8.1 | 14.5 | 5.5 |
| mulch + 2 wt % metal oxide composition | 1.75 | 0.5 | 16.1 | 14.5 | 1.1 |
| mulch + 5 wt % metal oxide composition | 0.75 | 6.0 | 0.6 | 12 | 11 |
| mulch + 5 wt % metal oxide composition | 1.75 | 7.0 | 1.2 | 12 | 5.5 |
| mulch + 5 wt % metal oxide composition | 1.75 | 3.5 | 2.3 | 12 | 4.5 |

TABLE 2-continued

| Material | Bed Height Feet | Flow cfm | Residence Time, sec. | ($H_2S$) in ppm | ($H_2S$) out ppm |
|---|---|---|---|---|---|
| mulch + 5 wt % metal oxide composition | 1.75 | 1.0 | 8.1 | 12 | 1.6 |
| mulch + 5 wt % metal oxide composition | 1.75 | 0.5 | 16.1 | 12 | 0.5 |
| mulch + 10 wt % metal oxide composition | 1.75 | 0.5 | 1.6 | 24 | 8 |
| mulch + 10 wt % metal oxide composition | 1.75 | 1 | 2.7 | 24 | 1.75 |
| mulch + 10 wt % metal oxide composition | 1.75 | 2 | 5.4 | 24 | 1 |
| mulch + 10 wt % metal oxide composition | 1.75 | 1.5 | 4.0 | 24 | 0.9 |
| mulch + 10 wt % metal oxide composition | 1.75 | 3 | 8.1 | 24 | 1 |
| mulch + 10 wt % metal oxide composition | 1.75 | 5 | 16.1 | 24 | <0.05 |
| mulch + 20 wt % metal oxide composition | 0.75 | 6.3 | 0.5 | 11 | 2.5 |
| mulch + 20 wt % metal oxide composition | 1.75 | 7.0 | 1.2 | 11 | 0.3 |
| mulch + 20 wt % metal oxide composition | 1.75 | 3.5 | 2.3 | 11 | <0.1 |
| mulch + 20 wt % metal oxide composition | 1.75 | 1.0 | 8.1 | 11 | <0.05 |
| mulch + 20 wt % metal oxide composition | 1.75 | 0.6 | 14.4 | 11 | <0.05 |

As can be seen, as the percentage of activated metal oxide increased, the time for removal decreased. Note also that the addition of a small amount of activated metal oxide resulted in near total elimination of the hydrogen sulfide. Thus, the activated metal oxide is important for removing sulfur.

Calculated removal times as a function of % iron oxide/cuprous oxide are shown in Table 3, below. As can be seen from the results in Table 3, hydrogen sulfide removal increases as the percentage of the activated metal oxide composition in the mulch increases. Using mulch with 2% (wt) iron oxide/cuprous oxide composition, 50% removal time was 4 seconds and 90% removal time was 13 seconds, whereas using mulch with 20% (wt) iron oxide/cuprous oxide composition 50% removal happens in 0.3 seconds and 90% removal in 1.2 seconds. Additionally, the required residence time is reduced, as the amount of activated metal oxide is increased.

TABLE 3

| % iron oxide/cuprous oxide composition | 50% removal time, seconds | 90% removal time, seconds |
|---|---|---|
| 0 | 35 | 117 |
| 2 | 4.0 | 13 |
| 5 | 1.7 | 5.6 |
| 10 | 0.9 | 2.9 |
| 20 | 0.3 | 1.2 |

Table 4 indicates the actual amount of iron oxide/cuprous oxide added to achieve the various weight percentages in this example.

TABLE 4

| % by wt iron oxide/cuprous oxide composition | Amount/Feet³ (cft), pounds | Amount/Yard³ (cyd), pounds |
|---|---|---|
| 2 | 0.25 | 6.9 |
| 5 | 0.64 | 17.2 |
| 10 | 1.27 | 34.3 |
| 20 | 2.54 | 68.6 |

Figure 7:
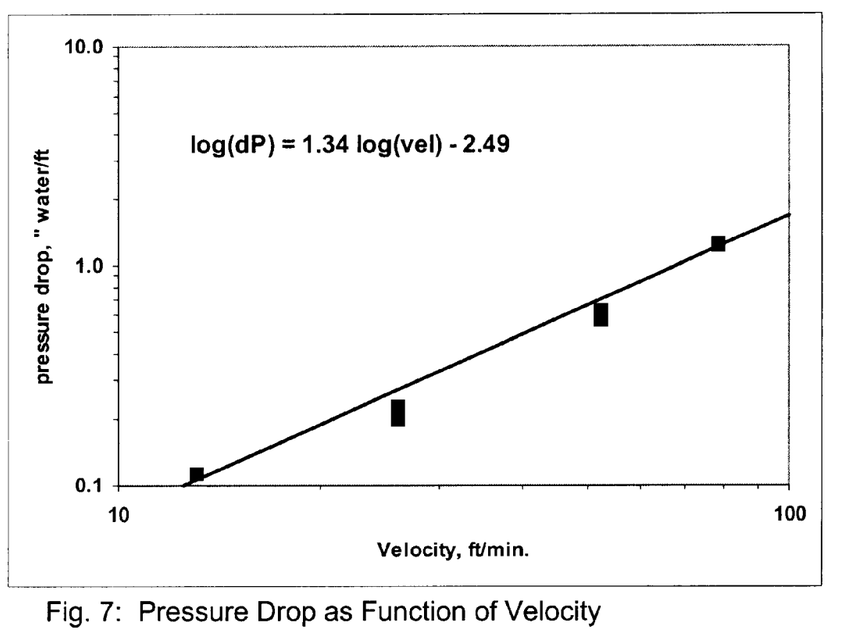

As shown by Table 5 and FIG. 7, the addition of the 10% iron oxide/cuprous oxide composition did not significantly effect the pressure drop of the mulch media. This is significant in that it indicates the mulch product is capable of removing hydrogen sulfide from contaminated sewage gas without having to add excess energy. If a drop in pressure had been shown, more energy would be required.

TABLE 5

| Velocity, ft/minute | Mulch pressure drop/ft, inches water | mulch + 10% pressure drop/ft, inches water |
|---|---|---|
| 13.0 | 0.11 | 0.11 |
| 26.1 | 0.20 | 0.23 |
| 52.2 | 0.57 | 0.63 |
| 78.2 | 1.24 | 1.26 |

Example 3

Field Test of Mulch Product Containing 43% (wt) Activated Metal Oxide

A field test was performed to determine the efficiency of removing odors from the wash sump of a pig barn. The mulch product contained activated metal oxide (FeO, CuO). 43% (wt) iron oxide/cuprous oxide composition was prepared following the procedure in Example 2. A 600 cubic feet per minute (cfm) blower attached to the wash sump was used to move the air from the wash sump, through a 4'×4' bed of the mulch product. This gave a bed contact time of approximately 4 seconds. Total sulfur and ammonia were measured at the inlet and outlet of the bed. The removal efficiency of the total sulfur was 88%, meaning the sulfur content of the air leaving the bed from the outlet contained 88% less sulfur than the air entering the bed from the inlet. The removal efficiency of the ammonia was 27%, meaning the air leaving the bed from the outlet contained 27% less ammonia then the air entering the bed at the inlet.

Example 4

Mulch Product Prepared Containing 50% by Weight of Activated Metal Oxide

A composition for treating sewage gases was formed by mixing 1,034 lbs. of bark mulch with 50% (wt) moisture with 1,000 lbs. of iron oxide and 20 lbs. of cuprous oxide. Then 236 lbs. of 410 clay was mixed, with 1.9 lbs. of Clary sage oil, 17.5 lbs. of green floral. To this, 60 lbs. of water and 35 lbs. of iron were added. Finally, the clay composition was mixed with the mulch composition to form a homogenous mulch product. As can be seen, hydrogen sulfide was totally removed in under 3 seconds (see Table 6).

TABLE 6

| (H₂S) in ppm | (H₂S) out ppm | cfm | Contact time, seconds |
|---|---|---|---|
| 50 | 0 | 1 | 2.3 |
| 50 | 0 | 2 | 1.2 |
| 50 | 0.9 | 3 | 0.8 |
| 50 | 6 | 5 | 0.5 |
| 50 | 11 | 7 | 0.3 |

Example 5

Mulch Product Prepared Containing 45% by Weight of Activated Metal Oxide

A composition for treating sewage gases was formed. An amount of bark mulch was mixed with an amount of dry iron oxide and cuprous oxide to form a mulch composition. The bark mulch was added in an amount equal to 900 lbs., the iron oxide was added in an amount equal to 1,000 lbs., and the cuprous oxide was added in an amount equal to 16 lbs. 236 lbs. of clay was mixed with odor counteractants and added to mulch composition. The odor counteractants were green floral and Clary sage oil. The green floral was added in an amount equal to 16.7 lbs., and the sage oil was added in an amount equal to 1.8 lbs. The clay/mulch composition was admixed until a homogenous mulch product was achieved. The percent of each constituent is listed in Table 7, below:

TABLE 7

| Constituent | Percentage |
|---|---|
| Mulch | 43.8 |
| Dry Iron Oxide | 44.24 |
| Cuprous Oxide | 0.71 |
| Clay | 10.44 |
| Green Floral | 0.74 |
| Clary Sage Oil | 0.08 |

Example 7

Comparison of Mulch Product Prepared Containing 50% by Weight of Activated Metal Oxide, plus 2% Essential Oil Suspended in Water, Sprayed on with Mulch Product Prepared Containing 50% by Weight of Activated Metal Oxide, plus 2% Essential Oil on Clay and Product Prepared Containing 2% Essential Oils on Clay.

Three separate compositions for treating sewage gases were compared. The first composition was formed by mixing 10 lbs. of bark mulch with 50% (wt) moisture with 10 lbs. of iron oxide and 0.2 lbs. of cuprous oxide to form a homogenous mulch/activated metal oxide composition. Next, 0.2 lbs. of Clary sage oil, 0.2 lbs. of green floral, and 1.0 lbs. of water were mixed together. Finally, the oil composition was mixed with the mulch/activated metal oxide composition to form a mulch product for treating sewage gases. The second composition was formed in the same way as the first composition except that 1.0 lbs. of large grained, calcined clay was used in place of the water. Finally, the third composition was formed by mixing 0.4 lbs. Clary sage oil and 0.4 lbs. green floral with 2 lbs. of large grained, calcined clay. All the products were separately placed in a 3.75" vessel and tested according to the procedure disclosed in Example 1. As seen in Table 8, the essential oil in water has effected the rate of hydrogen sulfide removal. The oil is reacting with activated metal oxide and interfering with its ability to remove the hydrogen sulfide. Thus higher levels of hydrogen sulfide are found in the compressed air leaving the vessel (see Table 8). In contrast, the addition of the 2% essential oil on clay had little to no effect on the mulch product's ability to remove hydrogen sulfide. The mulch product containing essential oil and clay contains 0 ppm of hydrogen sulfide in the compressed air at contact time 2.3 seconds, while the mulch product containing essential oil and water contains 3.4 ppm of hydrogen sulfide at contact time 2.3 seconds. The composition containing only 2% essential oil and clay had little to no effect on the amount of hydrogen sulfide in the contaminated air. As seen in Table 8, the amount of hydrogen sulfide in the compressed air entering the vessel containing essential oil and clay was 48 ppm. The compressed air leaving this vessel also contained 48 ppm of hydrogen sulfide at contact time 2.3 seconds, indicating neither the essential oil nor the clay effect the removal of hydrogen sulfide.

TABLE 8

| Constituent | (H₂S) in ppm | (H₂S) out ppm | cfm | Contact time, seconds |
|---|---|---|---|---|
| Mulch and Metal Oxide, Essential Oil on Water | 50 | 3.4 | 1 | 2.3 |
| Mulch and Metal Oxide, Essential Oil on Water | 50 | 19 | 2 | 1.2 |
| Mulch and Metal Oxide, Essential Oil on Water | 50 | 24 | 5.75 | 0.4 |
| Mulch and Metal Oxide, Essential Oil on Clay | 48 | 0 | 1 | 2.3 |
| Mulch and Metal Oxide, Essential Oil on Clay | 48 | 0 | 2 | 1.2 |
| Mulch and Metal Oxide, Essential Oil on Clay | 48 | 0.2 | 3.5 | 0.7 |
| Mulch and Metal Oxide, Essential Oil on Clay | 48 | 10 | 5.75 | 0.4 |
| Essential Oil on Clay | 48 | 45 | 0.5 | 4.6 |
| Essential Oil on Clay | 48 | 48 | 1 | 2.3 |

Thus, there has been shown and described a product, which fulfills all the objects and advantages sought therefore. It is apparent to those skilled in the art, however, that many changes, variations, modifications, and other uses and applications for the product are possible, and also such changes, variations, modifications, and other uses and applications which do not depart from the spirit and scope of the invention are deemed to be covered by the invention, which is limited only by the claims which follow.

What is claimed is:

1. A product for treating contaminated fluids, said product comprising:
   (a) an amount of a First carrier equal to between about 25% and about 98% by weight of said product;
   (b) an amount of metal oxide equal to between about 2% and about 75% by weight of said product;
   (c) an amount of odor counteractant equal to between about 0.1% and about 40% by weight of said product;
   (d) an amount of a second carrier for said odor counteractant equal to between about 1% and about 70% by weight of said product, said amount of odor counteractant in a mixture with said amount of carrier to substantially inhibit said amount of metal oxide from reacting with said amount of odor counteractant; and,
   (e) an amount of an agent which limits diffusion or said odor counteractant equal to between about 1% and about 75% by weight of said product.

2. The product of claim 1, wherein said odor counteractant is selected from the group consisting of essential oils, esters, mineral acids, organic acids, alkalines, and combinations thereof.

3. The product of claim 1, wherein said metal oxide is selected from the group consisting of iron oxide, iron hydroxide, zinc oxide, zinc hydroxide, and combinations thereof.

4. The product of claim 3, wherein said metal oxide includes an amount of activator, equal to between about 0.1% and about 20% by weight of said product, said activator selected from the group consisting of copper oxides, copper metals, copper carbonates, copper salts, copper alloys, platinum oxides, gold oxides, silver oxides, cadmium oxides, nickel oxides, palladium oxides, lead oxides, mercury oxides, tin oxides, cobalt oxides, manganese oxides, manganese carbonates, manganese metals, manganese salts, manganese alloys, and combinations thereof.

5. The product of claim 1, wherein said metal oxide is selected from the group consisting of manganese oxide, manganese hydroxide, and combinations thereof.

6. The product of claim 5, wherein said metal oxide includes an amount of activator, equal to between about 0.1% and about 20% by weight of said product, said activator selected from the group consisting of copper oxides, copper metals, copper carbonates, copper salts, copper alloys, platinum oxides, gold oxides, silver oxides, cadmium oxides, nickel oxides, palladium oxides, lead oxides, mercury oxides, tin oxides, cobalt oxides, and combinations thereof.

7. The product of claim 1, wherein said first carrier is mulch, said mulch selected from the group consisting of bark, wood products, compost, leaves, straw, soil, clays, carbon, limestone, shale, volcanic rock and combinations thereof.

8. The product of claim 1, wherein said second carrier for said odor counteractant is selected from the group consisting of clay, mulch, shale, carbon, porous styrofoam, porous ceramic, and combinations thereof.

9. The product of claim 1, wherein said agent is added in an amount which saturates said carrier for said odor counteractant.

10. The product of claim 1, wherein said agent is selected from the group consisting of water, glycols, diluents, and combinations thereof.

11. The product of claim 1, wherein the amount of said carrier is equal to between about 50% and about 75% by weight of said product.

12. The product of claim 1, wherein the amount of said metal oxide is equal to between about 35% and about 50% by weight of said product.

13. The product of claim 1, wherein the amount of said odor counteractant is equal to between about 1% and about 20% by weight of said product.

14. The product of claim 1, wherein the amount of said second carrier for said odor counteractant is equal to between about 5% and about 50% by weight of said product.

15. A method of using a product in ambient temperature to treat contaminated fluids, said method comprising placing said product in a vessel, said vessel constructed to allow the contaminated fluid to flow through said vessel, and thereby directly contacting said product, said product is comprised of a first carrier, an activated metal oxide, water, an odor counteractant, and a second carrier, said second carrier in a mixture with said odor counteractant to substantially inhibit said activated metal oxide from reacting with said odor counteractant.

16. The method of using a product of claim 15, wherein said product comprises:
(a) an amount or said First carrier equal to between about 25% and about 98% by weight of said product;
(b) an amount of activated metal oxide equal to between about 2% and about 75% by weight of said product;
(c) an amount of odor counteractant equal to between about 0.1% and about 40% by weight of said product;
(d) an amount of water equal to between about 1% by weight of said product and about 75% by weight of said product; and,
(e) an amount of said second carrier for said odor cotinteractant equal to between about 1% and about 70% by weight of said product.

17. The method of using a product of claim 15, wherein said product is used to treat contaminated sewage gas.

18. A mulch product for treating contaminated fluids, wherein said product comprises:
(a) an amount of bark mulch equal to between about 50% and about 75% by weight of said product;
(b) an amount of activated iron oxide equal to between about 35% and about 50% by weight of said product, said activated iron oxide includes an amount of activator equal to between about 0.25% and about 5% by weight of said product, said activator is a copper compound;
(c) an amount of clay equal to between about 5% and about 50% by weight of said product;
(d) an amount or water equal to between about 1% by weight of said product and 75% by weight of said product; and,
(e) an amount of odor counteractant equal to between about 1% and about 20% by weight of said product, said odor counteractant selected from the group consisting of essential oils, esters, mineral acids, organic acids, alkalines, and combinations thereof, said amount of odor counteractant in a mixture with said amount of clay to substantially inhibit said amount of iron oxide from reacting with said amount of odor counteractant.

19. A product for treating contaminated fluids, wherein said product chemically reduces hydrogen sulfide levels of contaminated fluids to non-detectable levels, and neutralizes malodors by contacting the contaminated fluids with reactive constituents of said product, said product comprising:
(a) an amount of carrier equal to between about 25% and about 98% by weight of said product;
(b) an amount of activated metal oxide equal to between about 2% and about 75% by weight of said product; and,
(c) an amount of odor counteractant composition in a mixture so as to be substantially inhibited from reacting with said amount of activated metal oxide.

20. The product for treating contaminated fluids of claim 19, wherein the hydrogen sulfide levels are reduced to between about 20% and about 99% of the hydrogen sulfide levels originally found in the contaminated fluids.

21. A product for treating contaminated fluids, said product comprising mulch, an activated metal oxide, an odor counteractant, and a carrier for said odor counteractant, said odor counteractant and said carrier for said odor counteractant in a mixture such that said odor counteractant is substantially inhibited from reacting with said activated metal oxide, and an agent, which limits diffusion or said odor counteractant.

* * * * *